United States Patent
Herfert et al.

(10) Patent No.: US 8,017,549 B2
(45) Date of Patent: Sep. 13, 2011

(54) SUPERABSORBENTS HAVING SUPERIOR PERMEABILITY AND CONVEYING PROPERTIES

(75) Inventors: Norbert Herfert, Altenstadt (DE); Martin Wendker, Wentorf (DE); Hermann Josef Feise, Kleinniedesheim (DE); Hanno Rüdiger Wolf, Heidelberg (DE); Bill Chiang, Charlotte, NC (US); Guy Thomas Woodrum, Midlothian, VA (US)

(73) Assignee: BASF SE, Ludwigshafen (DE)

( * ) Notice: Subject to any disclaimer, the term of this patent is extended or adjusted under 35 U.S.C. 154(b) by 71 days.

(21) Appl. No.: 12/447,103

(22) PCT Filed: Nov. 7, 2007

(86) PCT No.: PCT/EP2007/062016
§ 371 (c)(1), (2), (4) Date: Apr. 24, 2009

(87) PCT Pub. No.: WO2008/055935
PCT Pub. Date: May 15, 2008

(65) Prior Publication Data
US 2010/0093949 A1    Apr. 15, 2010

Related U.S. Application Data

(60) Provisional application No. 60/858,260, filed on Nov. 10, 2006.

(51) Int. Cl.
*B01J 20/26* (2006.01)
(52) U.S. Cl. ........ 502/402; 428/402; 524/430; 524/431; 524/436; 524/437; 524/442; 524/444; 524/445; 524/447; 524/451; 524/543; 524/556; 524/560; 525/194; 525/244; 526/317.1; 526/240; 526/318.2; 604/358
(58) Field of Classification Search .......... 428/402; 502/400, 401, 402; 524/430, 431, 436, 437, 524/442, 444, 445, 447, 451, 543, 556, 560; 525/194, 244; 526/317.1, 240, 318.2; 604/358
See application file for complete search history.

(56) References Cited

U.S. PATENT DOCUMENTS

| | | | |
|---|---|---|---|
| 5,994,440 A * | 11/1999 | Staples et al. ........... | 524/377 |
| 2005/0090586 A1 | 4/2005 | Kang et al. | |
| 2005/0113772 A1 | 5/2005 | La Fortune | |
| 2007/0293617 A1 | 12/2007 | Riegel et al. | |

FOREIGN PATENT DOCUMENTS

| | | |
|---|---|---|
| JP | 63039934 A | 2/1988 |
| WO | WO-94/22940 A1 | 10/1994 |
| WO | WO-97/37695 A1 | 10/1997 |
| WO | WO-98/48857 A1 | 11/1998 |
| WO | WO-00/62825 A2 | 10/2000 |
| WO | WO-01/45758 A1 | 6/2001 |
| WO | WO-02/060983 A2 | 8/2002 |
| WO | WO-03/057764 A2 | 7/2003 |
| WO | WO-2004/011047 A1 | 2/2004 |
| WO | WO-2004/018005 A1 | 3/2004 |
| WO | WO-2004/018006 A1 | 3/2004 |
| WO | WO-2004/069915 A2 | 8/2004 |
| WO | WO-2004/096303 A2 | 11/2004 |
| WO | WO-2005/011860 A2 | 2/2005 |
| WO | WO-2005/016393 A1 | 2/2005 |
| WO | WO-2005/061016 A1 | 7/2005 |
| WO | WO-2005/097881 A1 | 10/2005 |
| WO | WO-2005/108472 A1 | 11/2005 |
| WO | WO-2006/058683 A2 | 6/2006 |
| WO | WO-2008/118237 A1 | 10/2008 |

OTHER PUBLICATIONS

Graham, Edward T., et al., *Modern Superabsorbent Polymer Technology*, "Commercial Processes for the Manufacture of Superabsorbent Polymers" New York: John Wiley & Sons, Inc., 1998.
International Search Report in PCT/EP2007/062016 dated Oct. 10, 2009.

* cited by examiner

*Primary Examiner* — David W Wu
*Assistant Examiner* — Robert Jones, Jr.
(74) *Attorney, Agent, or Firm* — Marshall, Gerstein & Borun LLP

(57) ABSTRACT

A superabsorbent having superior permeability and conveying properties comprises a permeability enhancing agent and a cohesion control agent and has a free swell gel bed permeability of at least 15 Darcies and a Hausner ratio in the range of 1.18 to 1.34.

9 Claims, No Drawings

SUPERABSORBENTS HAVING SUPERIOR PERMEABILITY AND CONVEYING PROPERTIES

CROSS-REFERENCE TO RELATED APPLICATIONS

This is the U.S. national phase of International Application No. PCT/EP2007/062016, filed Nov. 7, 2007, which claims the benefit of U.S. Provisional Patent Application No. 60/858,260, filed Nov. 10, 2006.

The present invention relates to superabsorbents having superior permeability and conveying properties. In particular, the present invention relates to superabsorbents wherein the superabsorbent particles are coated with a permeability enhancing agent ("PEA") and a cohesion control agent ("CCA").

Superabsorbents are known. Superabsorbents are materials that are able to take up and retain several times their weight in water, possibly up to several hundred times their weight, even under moderate pressure. Absorbing capacity is usually lower for salt-containing solutions compared to distilled or otherwise de-ionised water. Typically, a superabsorbent has a centrifugal retention capacity ("CRC", method of measurement see hereinbelow) of at least 5 g/g, preferably at least 10 g/g and more preferably at least 15 g/g. Such materials are also commonly known by designations such as "high-swellability polymer", "hydrogel" (often even used for the dry form), "hydrogel-forming polymer", "water-absorbing polymer", "absorbent gel-forming material", "swellable resin", "water-absorbing resin" or the like. The materials in question are crosslinked hydrophilic polymers, in particular polymers formed from (co)polymerized hydrophilic monomers, graft (co)polymers of one or more hydrophilic monomers on a suitable grafting base, crosslinked ethers of cellulose or starch, crosslinked carboxymethylcellulose, partially crosslinked polyalkylene oxide or natural products that are swellable in aqueous fluids, examples being guar derivatives, of which water-absorbing polymers based on partially neutralized acrylic acid are most widely used. Superabsorbents are usually produced, stored, transported and processed in the form of dry powders of polymer particles, "dry" usually meaning less than 5 wt.-% water content. A superabsorbent transforms into a gel on taking up a liquid, specifically into a hydrogel when as usual taking up water. By far the most important field of use of superabsorbents is the absorbing of bodily fluids. Superabsorbents are used for example in diapers for infants, incontinence products for adults or feminine hygiene products. Examples of other fields of use are as water-retaining agents in market gardening, as water stores for protection against fire, for liquid absorption in food packaging or, in general, for absorbing moisture.

Processes for producing superabsorbents are also known. The acrylate-based superabsorbents which dominate the market are produced by radical polymerization of acrylic acid in the presence of a crosslinking agent (the "internal crosslinker"), usually in the presence of water, the acrylic acid being neutralized to some degree in a neutralization step conducted prior to or after polymerization, or optionally partly prior to and partly after polymerization, usually by adding a alkali, most often an aqueous sodium hydroxide solution. This yields a polymer gel which is comminuted (depending on the type of reactor used, comminution may be conducted concurrently with polymerization) and dried. Usually, the dried powder thus produced (the "base polymer") is surface crosslinked (also termed surface "post" crosslinked) by adding further organic or polyvalent cationic crosslinkers to generate a surface layer which is crosslinked to a higher degree than the particle bulk. Most often, aluminium sulphate is being used as polyvalent cationic crosslinker. Applying polyvalent metal cations to superabsorbent particles is sometimes not regarded as surface crosslinking, but termed "surface complexing" or as another form of surface treatment, although it has the same effect of increasing the number of bonds between individual polymer strands at the particle surface and thus increases gel particle stiffness as organic surface crosslinkers have. Organic and polyvalent cation surface crosslinkers can be cumulatively applied, jointly or in any sequence.

Surface crosslinking leads to a higher crosslinking density close to the surface of each superabsorbent particle. This addresses the problem of "gel blocking", which means that, with earlier types of superabsorbents, a liquid insult will cause swelling of the outermost layer of particles of a bulk of superabsorbent particles into a practically continuous gel layer, which effectively blocks transport of further amounts of liquid (such as a second insult) to unused superabsorbent below the gel layer. While this is a desired effect in some applications of superabsorbents (for example sealing underwater cables), it leads to undesirable effects when occurring in personal hygiene products. Increasing the stiffness of individual gel particles by surface crosslinking leads to open channels between the individual gel particles within the gel layer and thus facilitates liquids transport through the gel layer. Although surface crosslinking decreases the CRC or other parameters describing the total absorption capacity of a superabsorbent sample, it may well increase the amount of liquid that can be absorbed by hygiene product containing a given amount of superabsorbent.

Other means of increasing the permeability (to be precise, the "gel bed permeability", "GBP") of a superabsorbent are also known. These include admixing of superabsorbent with fibres such as fluff in a diaper core or admixing other components that increase gel stiffness or otherwise create open channels for liquid transportation in a gel layer. Usually, components increasing the GBP are referred to as permeability enhancing agents ("PEA").

Frederic L. Buchholz und Andrew T. Graham (Hrsg.) in: "Modern Superabsorbent Polymer Technology", J. Wiley & Sons, New York, U.S.A./Wiley-VCH, Weinheim, Germany, 1997, ISBN 0-471-19411-5, give a comprehensive overview over superabsorbents and processes for producing superabsorbents. In its section on additives for improved handling of solution-polymerised superabsorbents, this volume discloses that for humid environments, additives that reduce the rate of moisture absorption are of interest. One example is the combination of particulate silica with polyols or polyalkylene glycols for (co)polymers of poly(acrylamide). In its section on advanced products comprising surface crosslinking, aluminium acetate is disclosed as surface crosslinker.

WO 2004/096303 A2 discloses an absorbent structure comprising hydrophobic and hydrophilic fibres and superabsorber having a CRC of at least 25 g/g and a free swell GBP of at least $575 \cdot 10^{-9}$ cm$^2$. WO 2005/061 016 A1 teaches an absorbent structure comprising superabsorbent and hydrophilic fibres.

WO 2005/016 393 A1 describes a superabsorbent having a CRC of at least 20 g/g and a GBP under load of at least $200 \cdot 10^{-9}$ cm$^2$ or a free swell GBP of at least $2\,500 \cdot 10^{-9}$ cm$^2$. This superabsorbent is surface-treated with a water-soluble non-crosslinked cationic polymer such as polyvinyl amine.

WO 2004/069915 A2 discloses a composition of surface-crosslinked superabsorbents having a CRC of at lest 15 g/g and 0.01 to 5% of a permeability enhancing agent such as water-insoluble hydrophilic inorganic fine particles such as silica, or water-soluble polyvalent metal salts such as aluminium sulphate.

WO 2005/108472 A1 describes a superabsorbent which is surface-crosslinked by an organic crosslinker and a polyvalent metal salt admixed with an organic acid salt to decrease permeation of the metal into the particle bulk.

WO 00/62825 A2 teaches superabsorbent-containing composites comprised of superabsorbent particles and a coating material. The coating material is selected to selectively absorb bodily fluid components which may block water transport to superabsorbent particles, such as blood cells which are rapidly dewatered upon contact with superabsorbent particles, leaving a nearly impermeable layer of cell material around the superabsorbent particles. Examples of coating material are cellulosic materials such as microcrystalline cellulose powder or inorganic particles such as silica or clay.

WO 03/057764 A2 discloses superabsorbents having a highly crosslinked outer shell and having their surface covered by a fibrous coating material such as cellulose powder using an association agent such as water, organic solvents, film-forming materials or synthetic adhesives such as polyvinyl alcohol.

WO 2005/011860 A2 describes superabsorbents which are coated with fine particles by means of a thermoplastic adhesive. The fine particles may be superabsorbent fines such as undersized superabsorbent particles from the sieving operations during superabsorbent production or may be other organic particles such as cyclodextrines, cellulose or cellulose derivatives, or inorganic particles such as silica, clay, zeolithes or metal phosphates.

WO 98/48857 A1 discloses superabsorbent particles which are surface crosslinked by polyvalent metal cations such as Al, Fe, Zr, Mg and Zn ions and treated with a binder such as water mineral oil or polyols, for example propylene glycol, glycerine pr polyethylene glycol.

Japanese laid-open patent application JP 63/039934 teaches treating superabsorbents with an antidusting agent obtained by mixing a water-insoluble inorganic powder such as silica and organic compounds such as oxiethylene ether compounds or polyethylene glycol.

WO 2004/018005 A1 and WO 2004/018006 A1 describe clay-coated superabsorbent particles. WO 2005/097881 A1 and WO 02/060983 A2 relate to superabsorbents comprising water-insoluble phosphates, and WO 2006/058683 A2 to superabsorbents comprising insoluble metal sulphates.

WO 94/22940 A1 teaches de-dusting superabsorbents by application of a de-dusting agent such as lower aliphatic polyols of greater than about 200 average molecular weight of lower polyalkylene glycols of about 400 to about 6000 average molecular weight. Other suitable de-dusting agents are polyether polyols. The de-dusted superabsorbent may be further blended with flowability enhancers such as silica.

WO 97/37695 A1 discloses superabsorbents which are treated with quaternary ammonium salts to reduce caking. These superabsorbents may further comprise anti-caking agents One problem frequently associated with using permeability enhancing agents is that free flow and forced feeding characteristics of the superabsorbent are impeded. This means that conveying superabsorbent, in particular forced feeding of superabsorbents, for instance forced feeding superabsorbent to a superabsorbent processing device such as a diaper-forming machine by a screw apparatus, may become difficult, or, in a design where product is not force-fed, but intended to flow freely from an elevated transport container such as a big bag into a feeding device such as a diaper machine's superabsorbent feed hopper located below the superabsorbent transport container, free flow may be impeded. It is an object of the present invention to provide an improved superabsorbent. In particular, it is an object of the present invention to provide a superabsorbent having both superior gel bed permeability and superior conveying properties. It is a further object of this invention to provide a process for producing such superabsorbent, and another object is to provide liquid-absorbing products comprising such superabsorbent and processes for their production.

We have found that this object is achieved by a superabsorbent comprising a permeability enhancing agent and a cohesion control agent and having a free swell gel bed permeability of at least 15 Darcies and a Hausner ratio in the range of 1.18 to 1.34. We have further found a process for producing such superabsorbent, liquid-absorbing products comprising such superabsorbent and processes for their production.

The free swell gel bed permeability (free swell GBP) is an indicator of the ease of liquids transport through a layer of swollen superabsorbent, i.e. superabsorbent hydrogel. The test method for determining the free swell GBP is detailed below. The free swell GBP of the superabsorbent of this invention is generally at least 15 Darcies. Preferably, the free swell GBP is at least 20 Darcies and more preferably, it is at least 25 Darcies. Further examples of suitable free swell GPB values are values of at least 30 Darcies, at least 40 Darcies or at least 50 Darcies. There is no particular upper limit to this parameter in the context of this invention. The free swell GBP value can be increased by known means, in particular by adding more internal crosslinker, surface crosslinker, permeability enhancing agents or combinations thereof to almost any desired number. For contemporary applications, a free swell GBP of at most 200 Darcies will be sufficient in all but exceptional cases. A free swell GBP of at most 100 Darcies will be sufficient in most cases, and one of at most 60 Darcies will serve in most standard diaper applications.

The Hausner ratio, which is the ratio of packed bulk density to apparent bulk density, is an indicator of that part of void volume in a bed of superabsorbent powder that will be lost upon application of mechanical force as, for example, during forced feeding of the product. This influences the flowability (free flow) and the conveying (forced feeding) properties of the superabsorbent. Typically, a lower Hausner ratio indicates better flow-ability and worse conveying properties, and a higher Hausner ratio worse flowability and better conveying properties. The Hausner ratio of the inventive superabsorbent is generally at least 1.18, preferably at least 1.20, more preferred at least 1.24 and most preferred at least 1.26 and generally at most 1.34, preferably at most 1.33, more preferably at most 1.32 and most preferred at most 1.30. The Hausner ratio can be adjusted by adding an appropriate amount of cohesion control agent, and the appropriate amount for a given superabsorbent can easily be determined by few experiments.

The superabsorbent in the present invention is a superabsorbent capable of absorbing and retaining amounts of water equivalent to many times its own weight under a certain pressure. In general, it has a centrifugal retention capacity (CRC, method of measurement see hereinbelow) of at least 5 g/g, preferably at least 10 g/g and more preferably at least 15 g/g. Preferably, the superabsorbent is a crosslinked polymer based on partially neutralized acrylic acid, and more preferably it is surface postcrosslinked. A "superabsorbent" can also be a mixture of chemically different individual superabsorbents in that it is not so much the chemical composition which matters as the superabsorbing properties.

Processes for producing superabsorbents, including surface-postcrosslinked superabsorbents, are known. Synthetic superabsorbents are obtained for example by polymerization of a monomer solution comprising a) at least one ethylenically unsaturated acid-functional monomer,
b) at least one crosslinker,
c) optionally one or more ethylenically and/or allylically unsaturated monomers co-polymerizable with the monomer a), and
d) optionally one or more water-soluble polymers onto which the monomers a), b) and if appropriate c) can be at least partly grafted.

Suitable monomers a) are for example ethylenically unsaturated carboxylic acids, such as acrylic acid, methacrylic acid, maleic acid, fumaric acid and itaconic acid, or derivatives thereof, such as acrylamide, methacrylamide, acrylic esters and methacrylic esters. Acrylic acid and methacrylic acid are particularly preferred monomers. Acrylic acid is most preferable.

The monomers a) and especially acrylic acid comprise preferably up to 0.025% by weight of a hydroquinone half ether. Preferred hydroquinone half ethers are hydroquinone monomethyl ether (MEHQ) and/or tocopherols.

Tocopherol refers to compounds of the following formula:

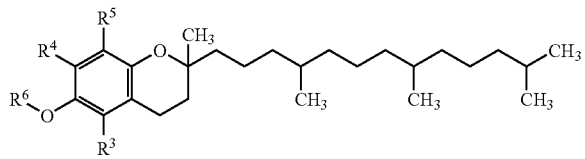

where $R^3$ is hydrogen or methyl, $R^4$ is hydrogen or methyl, $R^5$ is hydrogen or methyl and $R^4$ is hydrogen or an acid radical of 1 to 20 carbon atoms.

Preferred $R^6$ radicals are acetyl, ascorbyl, succinyl, nicotinyl and other physiologically tolerable carboxylic acids. The carboxylic acids can be mono-, di- or tricarboxylic acids.

Preference is given to alpha-tocopherol where $R^3=R^4=R^5$=methyl, especially racemic alpha-tocopherol. $R^6$ is more preferably hydrogen or acetyl. RRR-alpha-Tocopherol is preferred in particular.

The monomer solution comprises preferably not more than 130 weight ppm, more preferably not more than 70 weight ppm, preferably not less than 10 weight ppm, more preferably not less than 30 weight ppm and especially about 50 weight ppm of hydroquinone half ether, all based on acrylic acid, with acrylic acid salts being arithmetically counted as acrylic acid. For example, the monomer solution can be produced using an acrylic acid having an appropriate hydroquinone half ether content.

Crosslinkers b) are compounds having at least two polymerizable groups which can be free-radically interpolymerized into the polymer network. Useful crosslinkers b) include for example ethylene glycol dimethacrylate, diethylene glycol diacrylate, allyl methacrylate, trimethylolpropane triacrylate, triallylamine, tetraallyloxyethane as described in EP 530 438 A1, di- and triacrylates as described in EP 547 847 A1, EP 559 476 A1, EP 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and WO 04/013 064 A2, or crosslinker mixtures as described for example in DE 195 43 368 A1, DE 196 46 484 A1, WO 90/15830 A1 and WO 02/032962 A2.

Useful crosslinkers b) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP 343 427 A2. Useful crosslinkers b) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention may utilize di(meth)acrylates of polyethylene glycols, the polyethylene glycol used having a molecular weight between 300 and 1000.

However, particularly advantageous crosslinkers b) are di- and triacrylates of 3- to 15-tuply ethoxylated glycerol, of 3- to 15-tuply ethoxylated trimethylolpropane, of 3- to 15-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixedly ethoxylated or propoxylated glycerol, of 3-tuply mixedly ethoxylated or propoxylated trimethylolpropane, of 15-tuply ethoxylated glycerol, of 15-tuply ethoxylated trimethylolpropane, of 40-tuply ethoxylated glycerol, of 40-tuply ethoxylated trimethylolethane and also of 40-tuply ethoxylated trimethylolpropane.

Very particularly preferred for use as crosslinkers b) are diacrylated, dimethacrylated, triacrylated or trimethacrylated multiply ethoxylated and/or propoxylated glycerols as described for example in WO 03/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual contents (typically below 10 weight ppm) in the water-absorbing polymer and the aqueous extracts of the water-absorbing polymers produced therewith have an almost unchanged surface tension (typically at least 0.068 N/m) compared with water at the same temperature.

Examples of ethylenically unsaturated monomers c) which are copolymerizable with the monomers a) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers d) include polyvinyl alcohol, polyvinylpyrrolidone, starch, starch derivatives, polyethyleneimines, polyglycols, polymers formally constructed wholly or partly of vinylamine monomers, such as partially or completely hydrolyzed polyvinylamide (so-called "polyvinylamine") or polyacrylic acids, preferably polyvinyl alcohol and starch.

The polymerization is optionally carried out in the presence of customary polymerization regulators. Suitable polymerization regulators are for example thio compounds, such as thioglycolic acid, mercapto alcohols, for example 2-mercaptoethanol, mercaptopropanol and mercaptobutanol, dodecyl mercaptan, formic acid, ammonia and amines, for example ethanolamine, diethanolamine, triethanolamine, triethylamine, morpholine and piperidine.

The monomers (a), (b) and optionally (c) are (co)polymerized with each other in the presence of the water-soluble polymers d), in 20% to 80%, preferably 20% to 50% and especially 30% to 45% by weight aqueous solution in the presence of polymerization initiators. Useful polymerization initiators include all compounds that disintegrate into free radicals under the polymerization conditions, examples being peroxides, hydroperoxides, hydrogen peroxide, persulfates, azo compounds and the so-called redox initiators. The use of water-soluble initiators is preferred. It is advantageous in some cases to use mixtures of various polymerization initiators, examples being mixtures of hydrogen peroxide and sodium or potassium peroxodisulfate. Mixtures of hydrogen peroxide and sodium peroxodisulfate can be used in any desired ratio. Suitable organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, tert-butyl per-3,5,5-trimethylhexanoate and tert-amyl perneodecanoate. Further suitable polymerization initiators are azo initiators, for example 2,2'-azobis(2-amidinopropane) dihydrochloride, 2,2'-azobis(N,N-dimethylene)-isobutyramidine dihydrochloride, 2-(carbamoylazo)isobutyronitrile and 4,4'-azobis(4-cyanovaleric acid). The polymerization initiators mentioned are used in customary amounts, for example in amounts of from 0.01 to 5 mol %, preferably 0.1 to 2 mol %, based on the monomers to be polymerized.

The redox initiators comprise, as oxidizing component, at least one of the above-indicated per compounds and a reducing component, for example ascorbic acid, glucose, sorbose, ammonium bisulfite, ammonium sulfite, ammonium thiosulfate, ammonium hyposulfite, ammonium pyrosulfite, ammonium sulfide, alkali metal bisulfite, alkali metal sulfite, alkali metal thiosulfate, alkali metal hyposulfite, alkali metal pyrosulfite, alkali metal sulfide, metal salts, such as iron(II) ions or silver ions, sodium hydroxy-methylsulfoxylate, or sulfinic acid derivatives. The reducing component of the redox initiator is preferably ascorbic acid or sodium pyrosulfite. $1 \cdot 10^{-5}$ to 1 mol % of the reducing component of the redox initiator and $1 \cdot 10^{-5}$ to 5 mol % of the oxidizing component are used based on the amount of monomers used in the polymerization. Instead of the oxidizing component or in addition it is also possible to use one or more watersoluble azo initiators.

A redox initiator consisting of hydrogen peroxide, sodium peroxodisulfate and ascorbic acid is preferably used. These components are used for example in the concentrations of $1 \cdot 10^{-2}$ mol % of hydrogen peroxide, 0.084 mol % of sodium peroxodisulfate and $2.5 \cdot 10^{-3}$ mol % of ascorbic acid, based on the monomers.

It is also possible to initiate the polymerization by the numerous other known means to initiate polymerizations. On example is initiating polymerization by irradiating with radiation of sufficiently high energy, in particular ultraviolet light. Usually, when initiating polymerization by ultraviolet light, compounds are added which decompose into radicals upon irradiation by ultraviolet light. Examples of such compounds are 2-hydroxi-2-methyl-1-phenyl-1-propanone and/or alpha,-alpha-dimethoxi-alpha-phenylacetophenone.

The aqueous monomer solution may comprise the initiator in dissolved or dispersed form. However, the initiators may also be added to the polymerization reactor separately from the monomer solution.

The preferred polymerization inhibitors require dissolved oxygen for optimum effect. Therefore, the polymerization inhibitors can be freed of dissolved oxygen prior to polymerization, by inertization, i.e., by flowing an inert gas, preferably nitrogen, through them. This is accomplished by means of inert gas, which can be introduced concurrently, countercurrently or at entry angles in between. Good commixing can be achieved for example with nozzles, static or dynamic mixers or bubble columns. The oxygen content of the monomer solution is preferably lowered to less than 1 weight ppm and more preferably to less than 0.5 weight ppm prior to polymerization. The monomer solution is optionally passed through the reactor using an inert gas stream.

The preparation of a suitable polymer as well as further suitable hydrophilic ethylenically unsaturated monomers a) are described for example in DE 199 41 423 A1, EP 686 650 A1, WO 01/45758 A1 and WO 03/104300 A1.

Superabsorbents are typically obtained by addition polymerization of an aqueous monomer solution and optionally a subsequent comminution of the hydrogel. Suitable methods of making are described in the literature. Superabsorbents are obtained for example by gel polymerization in the batch process or tubular reactor and subsequent comminution in meat grinder, extruder or kneader, as described for example in EP 445 619 A2 and DE 198 46 413 A1;

polymerization in kneader with continuous comminution by contrarotatory stirring shafts for example, as described for example in WO 01/38402 A1;

polymerization on belt and subsequent comminution in meat grinder, extruder or kneader, as described for example in EP 955 086 A2, DE 38 25 366 A1 or U.S. Pat. No. 6,241,928;

emulsion polymerization, which produces bead polymers having a relatively narrow gel size distribution, as described for example in EP 457 660 A1;

in situ polymerization on a woven fabric layer which, usually in a continuous operation, has previously been sprayed with aqueous monomer solution and subsequently been subjected to a photopolymerization, as described for example in WO 02/94328 A2, WO 02/94329 A1.

The cited references are expressly incorporated herein for details of process operation. The reaction is preferably carried out in a kneader or on a belt reactor.

Continuous gel polymerization is the economically preferred and therefore currently customary way of manufacturing superabsorbents. The process of continuous gel polymerization is carried out by first producing a monomer mixture by admixing the acrylic acid solution with the neutralizing agent, optional comonomers and/or further auxiliary materials at different times and/or locations and then transferring the mixture into the reactor or preparing the mixture as an initial charge in the reactor. The initiator system is added last to start the polymerization. The ensuing continuous process of polymerization involves a reaction to form a polymeric gel, i.e., a polymer swollen in the polymerization solvent—typically water—to form a gel, and the polymeric gel is already comminuted in the course of a stirred polymerization. The polymeric gel is subsequently dried, if necessary, and also chipped ground and sieved and is transferred for further surface treatment.

The acid groups of the hydrogels obtained are partially neutralized in an acid neutralization step, generally to an extent of at least 25 mol %, preferably to an extent of at least 50 mol % and more preferably at least 60 mol % and generally to an extent of not more than 85 mol %, preferably not more than 80 mol %, and more preferably not more than 75 mol %.

Neutralization can also be carried out after polymerization, at the hydrogel stage. But it is also possible to carry out the neutralization to the desired degree of neutralization wholly or partly prior to polymerization. In the case of partial neutralization and prior to polymerization, generally at least 10 mol %, preferably at least 15 mol % and also generally not more than 40 mol %, preferably not more than 30 mol % and more preferably not more than 25 mol % of the acid groups in the monomers used are neutralized prior to polymerization by adding a portion of the neutralizing agent to the monomer solution. The desired final degree of neutralization is in this case only set toward the end or after the polymerization, preferably at the level of the hydrogel prior to its drying. The monomer solution is neutralized by admixing the neutralizing agent. The hydrogel can be mechanically comminuted in the course of the neutralization, for example by means of a meat grinder or comparable apparatus for comminuting gellike masses, in which case the neutralizing agent can be sprayed, sprinkled or poured on and then carefully mixed in. To this end, the gel mass obtained can be repeatedly meat-grindered for homogenization.

Neutralization of the monomer solution to the desired final degree of neutralization prior to polymerization by addition of the neutralizing agent or conducting the neutralization after polymerization is usually simpler than neutralization partly prior to and partly after polymerization and therefore is preferred.

The as-polymerized gels are optionally maintained for some time, for example for at least 30 minutes, preferably at least 60 minutes and more preferably at least 90 minutes and also generally not more than 12 hours, preferably for not more than 8 hours and more preferably for not more than 6 hours at a temperature of generally at least 50° C. and preferably at least 70° C. and also generally not more than 130° C. and preferably not more than 100° C., which further improves their properties in many cases.

The neutralized hydrogel is then dried with a belt or drum dryer until the residual moisture content is preferably below 15% by weight and especially below 10% by weight, the water content being determined by EDANA (European Disposables and Nonwovens Association) recommended test method No. 430.2-02 "Moisture content". The dry superabsorbent consequently contains up to 15% by weight of moisture and preferably not more than 10% by weight. The decisive criterion for classification as "dry" is in particular a sufficient flowability for handling as a powder, for example for pneumatic conveying, pack filling, sieving or other processing steps involved in solids processing technology. Optionally, however, drying can also be carried out using a fluidized bed dryer or a heated ploughshare mixer. To obtain particularly colourless products, it is advantageous to dry this gel by ensuring rapid removal of the evaporating water. To this end, dryer temperature must be optimized, air feed and removal has to be policed, and at all times sufficient venting has to be ensured. Drying is naturally all the more simple— and the product all the more colourless—when the solids content of the gel is as high as possible. The solvent fraction at addition polymerization is therefore set such that the solid content of the gel prior to drying is therefore generally at least 20% by weight, preferably at least 25% by weight and more preferably at least 30% by weight and also generally not more than 90% by weight, preferably not more than 85% by weight and more preferably not more than 80% by weight. It is particularly advantageous to vent the dryer with nitrogen or some other nonoxidizing inert gas. Optionally, however, simply just the partial pressure of oxygen can be lowered during drying to prevent oxidative yellowing processes. But in general adequate venting and removal of the water vapour will likewise still lead to an acceptable product. A very short drying time is generally advantageous with regard to colour and product quality.

The dried hydrogel (which is no longer a gel (even though often still called that) but a dry polymer having superabsorbing properties, which comes within the term "superabsorbent") is preferably ground and sieved, useful grinding apparatus typically including roll mills, pin mills, hammer mills, cutting mills or swing mills. The particle size of the sieved, dry hydrogel is preferably below 1000 μm, more preferably below 900 μm and most preferably below 850 μm and preferably above 80 μm, more preferably above 90 μm and most preferably above 100 μm.

Very particular preference is given to a particle size (sieve cut) in the range from 106 to 850 μm. Particle size is determined according to EDANA (European Disposables and Nonwovens Association) recommended test method No. 420.2-02 "Particle size distribution".

The dry superabsorbing polymers thus produced are typically known as "base polymers" and are then preferably surface postcrosslinked. Surface postcrosslinking can be accomplished in a conventional manner using dried, ground and classified polymeric particles. For surface postcrosslinking, compounds capable of reacting with the functional groups of the base polymer by crosslinking are applied, usually in the form of a solution, to the surface of the base polymer particles. Suitable postcrosslinkling agents are for example:

di- or polyepoxides, for example di- or polyglycidyl compounds such as phosphonic acid diglycidyl ether, ethylene glycol diglycidyl ether, bischlorohydrin ethers of polyalkylene glycols, alkoxysilyl compounds, polyaziridines, compounds comprising aziridine units and based on polyethers or substituted hydrocarbons, for example bis-N-aziridinomethane, polyamines or polyamidoamines and also their reaction products with epichlorohydrin, polyols such as ethylene glycol, 1,2-propanediol, 1,4-butanediol, glycerol, methyltriglycol, polyethylene glycols having an average molecular weight Mw of 200-10 000, di- and polyglycerol, pentaerythritol, sorbitol, the ethoxylates of these polyols and also their esters with carboxylic acids or carbonic acid such as ethylene carbonate or propylene carbonate, carbonic acid derivatives such as urea, thiourea, guanidine, dicyandiamide, 2-oxazolidinone and its derivatives, bisoxazoline, polyoxazolines, di- and polyisocyanates, di- and poly-N-methylol compounds such as for example methylenebis(N-methylolmethacrylamide) or melamine-formaldehyde resins, compounds having two or more blocked isocyanate groups such as for example trimethylhexamethylene diisocyanate blocked with 2,2,3,6-tetrannethylpiperidin-4-one.

If necessary, acidic catalysts can be added, examples being p-toluenesulfonic acid, phosphoric acid, boric acid or ammonium dihydrogenphosphate.

Particularly suitable postcrosslinking agents are di- or polyglycidyl compounds such as ethylene glycol diglycidyl ether, the reaction products of polyamidoamines with epichlorohydrin, 2-oxazolidinone and N-hydroxyethyl-2-oxazolidinone.

Surface postcrosslinking (often just "postcrosslinking") is typically carried out by spraying a solution of the surface postcrosslinker (often just "postcrosslinker") onto the hydrogel or the dry base polymer powder.

The solvent used for the surface postcrosslinker is a customary suitable solvent, examples being water, alcohols, DMF. DMSO and also mixtures thereof. Particular preference is given to water and water-alcohol mixtures, examples being water-methanol, water-1,2-propanediol, water-2-propanol and water-1,3-propanediol.

The spraying with a solution of the postcrosslinker is preferably carried out in mixers having moving mixing implements, such as screw mixers, paddle mixers, disk mixers, plowshare mixers and shovel mixers. Particular preference is given to vertical mixers and very particular preference to plowshare mixers and shovel mixers. Useful and known mixers include for example Lödige®, Bepex®, Nauta®, Processall® and Schugi® mixers. Very particular preference is given to high speed mixers, for example of the Schugi-Flexomix® or Turbolizer® type.

The spraying with the crosslinker solution can be optionally followed by a thermal treatment step, essentially to effect the surface-postcrosslinking reaction (yet usually just referred to as "drying"), preferably in a downstream heated mixer ("dryer") at a temperature of generally at least 50° C., preferably at least 80° C. and more preferably at least 80° C. and also generally not more than 300° C., preferably not more than 250° C. and more preferably not more than 200° C. The average residence time (i.e., the averaged residence time of the individual particles of superabsorbent) in the dryer of the superabsorbent to be treated is generally at least 1 minute, preferably at least 3 minutes and more preferably at least 5 minutes and also generally not more than 6 hours, preferably 2 hours and more preferably not more than 1 hour. As well as the actual drying taking place, not only any products of scissioning present but also solvent fractions are removed. Thermal drying is carried out in customary dryers such as tray dryers, rotary tube ovens or heatable screws, preferably in contact dryers. Preference is given to the use of dryers in which the product is agitated, i.e., heated mixers, more preferably shovel dryers and most preferably disk dryers. Bepex® dryers and Nara® dryers are suitable dryers for example. Fluidized bed dryers can also be used. But drying can also take place in the mixer itself, by heating the jacket or blowing a preheated gas such as air into it. But it is also possible for example to utilize an azeotropic distillation as a drying process. The crosslinking reaction can take place not only before but also during drying.

The polymer is treated with a permeability enhancing agent. It is possible to treat the polymer simultaneously with surface crosslinker and permeability enhancing agent, but it is preferred to treat a surface-crosslinked polymer with a permeability enhancing agent.

The permeability agent can be any agent that increases gel bed permeability. It is preferably at least one permeability enhancing agent selected from the group formed by:
  particulate inorganic or organic solids;
  cationic polymers; and
  water-soluble polyvalent metal salts.

It is possible to apply more than one type of permeability enhancing agent. In general, the total amount of permeability enhancing agent added to a particular superabsorbent is adjusted to achieve the desired free swell GBP. Typically, permeability enhancing agents are used in an amount of at least 0.05 wt.-%, preferably at least 0.1 wt.-%, more preferably at least 0.3 wt.-% and generally at most 5 wt.-%, preferably at most 1.5 wt.-% and more preferably at most 1 wt.-%, in each case based on the total weight of the material.

Suitable particulate inorganic solids are superabsorbent permeability-enhancing particulate solids that are chemically inert with respect to a superabsorbent. Suitable permeability-enhancing particulate solids are well known in the art. Examples of suitable particulate inorganic solids include silicates and alumosilicates having a band, chain or sheet structure (such as montmorillonite, kaolinite, talc), zeolithes, silica, alumina, titanium dioxide, iron (II)oxide), magnesium carbonate, calcium carbonate, calcium phosphate, calcium sulphate and barium sulphate. Examples of suitable particulate organic solids include active carbon, superabsorbent fine particles such as undersized particles from sieving operations during superabsorbent production, cyclodextrines, cellulose and cellulose derivatives. Silica is preferred, in particular hydrophobic silica. The particle size of powders to be used as permeability enhancing agent is on a nanometer to micrometer scale. Preferably, the particle size is small enough as to yield a coating or partial coating of permeability enhancing agent on the superabsorbent particle surface. Generally, the particle size (measured as "d50", usually by laser diffraction, which means that 50% of the particles are smaller than the recorded value and 50% larger) is at least 0.1 micron, preferably at least 0.5 micron and more preferably at least 1 micron and generally at most 500 micron, preferably at most 200 micron and more preferably at most 100 micron. The individual powder particles of such substances are usually comprised of much smaller, so-called primary particles. A typical size of primary particles is on a nanometer scale. One example of a suitable particulate solid is hydrophobic silica having a d50 particle size of about 10 micron.

Particulate solid permeability enhancing agents may be applied by spraying a solution or dispersion thereof in water or an organic solvent onto the superabsorbent polymer powder while agitating and subsequent drying. It is also possible and preferred in case of insoluble or hydrophobic permeability enhancing agents to mix dry superabsorbent polymer powder and dry permeability enhancing agent.

Examples of suitable cationic polymers include polyalkenepolyamines, which are polymers formally constructed wholly or partly of vinylamine monomers, such as partially or completely hydrolyzed polyvinylamide (so-called "polyvinylamine") whose amine groups are always—even at very high pH values—partly present in a state of protonation to ammonium groups, cationic derivatives of polyacrylamides, polyethyleneimines, polyquaternary amines, for example condensation products of hexamethylenediamine, dimethylamine and epichlorohydrin, copolymers of hydroxyethylcellulose and diallyldimethylammonium chloride, copolymers of acrylamide and β-methacryloxyethyltrimethylammonium chloride, hydroxycellulose reacted with epichlorohydrin and then quaternized with trimethylamine, homopolymers of diallyldimethylammonium chloride or addition products of epichlorohydrin with amidoamines. Polyquaternary amines may further be synthesized by reaction of dimethyl sulfate with polymers, such as polyethyleneamines, copolymers of vinylpyrrolidone and dimethylaminoethyl methacrylate or copolymers of ethyl methacrylate and diethylaminoethyl methacrylate. Polyquaternary amines are available in a wide molecular range.

These permeability enhancing agents can also have the form of a crosslinked, cationic sheath, generated either by reacting reagents capable of forming a network, for example addition products of epichlorohydrin with polyamidoamines, or by applying cationic polymers capable of reacting with an added crosslinker, for example polyamines or polyimines combined with polyepoxides, multifunctional esters multifunctional acids or multifunctional (meth)acrylates. It is also possible to use any multifunctional amines having primary or secondary amino groups, for example polyethyleneimine, polyallylamine, polylysine, preferably polyvinylamine. Further examples of polyamines are ethylenediamine, diethylenetriamine, triethylenetetramine, tetraethylenepentamine, pentaethylenehexamine and polyethyleneimines and also polyamines having molar masses of up to 4 000 000 in each case.

Water-soluble polyvalent metal salts comprise bi- or more highly valent ("polyvalent") metal cations capable of reacting with the acid groups of the polymer to form complexes. Examples of polyvalent cations are or metal cations such as $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{2+}$, $Zn^{2+}$, $Y^{3+}$, $Zr^{4+}$, $La^{3+}$, $Ce^{4+}$, $Hf^{4+}$, and $Au^{3+}$. Preferred metal cations are $Mg^{2+}$, $Ca^{2+}$, $Al^{3+}$, $Ti^{4+}$, $Zr^{4+}$ and $La^{3+}$, and particularly preferred metal cations are $Al^{3+}$, $Ti^{4+}$ and $Zr^{4+}$. The metal cations can be used not only alone but also in admixture with each other. Of the metal cations mentioned, any metal salt can be used that has sufficient solubility in the solvent to be used. Metal salts with weakly complexing anions such as for example chloride, nitrate and sulphate, hydrogen sulphate, carbonate, hydrogen carbonate, nitrate, phosphate, hydrogen phosphate, dihydrogen phosphate and carboxylate, such as acetate and lactate, are particularly suitable. It is particularly preferred to use aluminum sulfate.

The treatment of the superabsorbent polymer with solution of a polyvalent cation is carried out in the same way as that with surface postcrosslinker, including the selective drying step. Useful solvents for the metal salts include water, alcohols, DMF, DMSO and also mixtures thereof. Particular preference is given to water and water-alcohol mixtures such as for example water-methanol, water-1,2-propanediol, water-2-propanol and water-1,3-propanediol.

In a preferred embodiment, permeability is enhanced by applying aluminium(III), most preferably in the form of aluminium sulphate, and silica as the permeability enhancing agent.

In a preferred embodiment of the present invention, the permeability enhancing agent is applied to a superabsorbent that is surface crosslinked, or simultaneously with surface crosslinking, or partly simultaneously and partly after surface crosslinking. For example, a suitable method of applying a permeability enhancing agent is applying a polyvalent metal cation such as $Al^{3+}$ simultaneously with a surface crosslinker and applying a particulate solid such as silica after the step of surface crosslinking, for example during a cooling step conducted after drying the surface crosslinked product.

After any drying step, it is advantageous but not absolutely necessary to cool the product after drying. Cooling can be carried out continuously or discontinuously, conveniently by conveying the product continuously into a cooler downstream of the dryer. Any apparatus known for removing heat from pulverulent solids can be used, in particular any apparatus mentioned above as a drying apparatus, provided it is supplied not with a heating medium but with a cooling medium such as for example with cooling water, so that heat is not introduced into the superabsorbent via the walls and, depending on the design, also via the stirrer elements or other heat-exchanging surfaces, but removed from the superabsorbent. Preference is given to the use of coolers in which the product is agitated, i.e., cooled mixers, for example shovel coolers, disk coolers or paddle coolers, for example Nara® or Bepex® coolers. The superabsorbent can also be cooled in a fluidized bed by blowing a cooled gas such as cold air into it. The cooling conditions are set such that a superabsorbent having the temperature desired for further processing is obtained. Typically, the average residence time in the cooler will be in general at least 1 minute, preferably at least 3 minutes and more preferably at least 5 minutes and also in general not more than 6 hours, preferably 2 hours and more preferably not more than 1 hour, and cooling performance will be determined such that the product obtained has a temperature of generally at least 0° C., preferably at least 10° C. and more preferably at least 20° C. and also generally not more than 100° C., preferably not more than 80° C. and more preferably not more than 60° C.

The superabsorbent is also treated with a cohesion control agent. A cohesion control agent is a non-aqueous liquid having a viscosity of at least 20 mPas, preferably at least 30 mPas, more preferably at least 40 mPas and most preferably at least 80 mPas, and generally not more than 1 000 mPas, preferably not more than 700 mPas, all at 20° C.

A suitable cohesion control agent is at least one agent of this viscosity selected from the group formed by:
  alcohols
  poly glycols
  silicon oils
  hydrophilic modified silicon oils
  paraffin oils These cohesion control agents and methods of adding them to superabsorbent are known per se. Examples of suitable alcohols are 1,2-propylene glycol, 1,3-propane diol, 1,2-, 1,3- and 1,4-butandiol or glycerine. Examples of suitable polyglycols are poly ethylene glycols, poly propylene glycols or poly butylene glykols. Generally, these have a molecular mass of not more than 5 000 g/mol, preferably not more than 3 000 g/mol and more preferably not more than 2000 g/mol.

Preferred cohesion control agents are 1,2-propylene glycol, poly ethylene glycols with an average molecular weight of less than 1 500 g/mol, silicon oil, and hydrophilic modified silicon oil.

It is possible to apply more than one type of cohesion control agent. In general, the total amount of cohesion control agent added to a particular superabsorbent is adjusted to achieve the desired Hausner ratio, and to obtain a product that flows freely from a transport container such as a "big bag" into a feeding device. The optimum quantity of cohesion control agent depends on the type of superabsorbent and in particular on the type and amount of permeability enhancing agent. Typically, cohesion control agents are used in an amount of at least 100 wt.-ppm, preferably at least 200 wt.-ppm, more preferably at least 300 wt.-ppm and generally at most 5 000 wt.-ppm, preferably at most 3 000 wt.-ppm and more preferably at most 1 500 wt.-ppm, in each case based on the total weight of material.

The cohesion control agent is preferably applied to the polymer after surface crosslinking, and after the addition of permeability enhancing agent. Most preferably, the cohesion control agent is added after the heat treatment step applied during surface crosslinking or after a heat treatment step applied in the course of addition of permeability enhancing agent. It may be convenient to apply the cohesion control agent during a cooling step following surface crosslinking and addition of permeability enhancing agent, depending on whether the cooler provides sufficient mixing quality. It is always possible to add the cohesion control agent in a separate step, usually in a mixer, and preferably after surface crosslinking and adding a permeability enhancing agent. In some cases, it is possible to apply the cohesion control agent during surface crosslinking or addition of permeability enhancing agent, contingent upon inertness of the cohesion control agent during surface crosslinking.

Adding cohesion control agent usually necessitates no subsequent heating step. If a heating step should be necessary due to some special circumstances, care has to be taken to avoid any temperatures high enough for reaction between the cohesion control agent and the polymer.

Optionally, the superabsorbent is provided with further customary additives and auxiliary materials to influence storage or handling properties. Examples thereof are colorations, opaque additions to improve the visibility of swollen gel, which is desirable in some applications, surfactants or the like. Similarly, a final water content can be set for the superabsorbent, if desired, by adding water. These additives and auxiliary materials can each be added in separate processing steps, but one convenient method may be to add them to the superabsorbent in the cooler, for example by spraying the superabsorbent with a solution or adding them in finely divided solid or in liquid form, if this cooler provides sufficient mixing quality.

The surface-crosslinked superabsorbent treated with permeability enhancing agent and cohesion control agent is optionally ground and/or sieved in a conventional manner. Grinding is typically not necessary, but the sieving out of agglomerates which are formed or undersize is usually advisable to set the desired particle size distribution for the product. Agglomerates and undersize are either discarded or preferably returned into the process in a conventional manner and at a suitable point; agglomerates after comminution. The superabsorbent particle size is preferably not more than 1000 μm, more preferably not more than 900 μm, most preferably not more than 850 μm, and preferably at least 80 μm, more preferably at least 90 μm and most preferably at least 100 μm. Typical sieve cuts are for example 106 to 850 μm or 150 to 850 μm.

We have further found superabsorbent produced by the process of the present invention and hygiene articles comprising the superabsorbent produced by the process of the present invention. Hygiene articles in accordance with the present invention are for example those intended for use in mild or severe incontinence, such as for example inserts for severe or mild incontinence, incontinence briefs, also diapers, training pants for babies and infants or else feminine hygiene articles such as liners, sanitary napkins or tampons. Hygiene articles of this kind are known. The hygiene articles of the present invention differ from known hygiene articles in that they comprise the superabsorbent of the present invention. We have also found a process for producing hygiene articles, this process comprising utilizing at least one superabsorbent of the present invention in the manufacture of the hygiene article in question. Processes for producing hygiene articles using superabsorbent are otherwise known.

The present invention further provides for the use of the composition of the present invention in training pants for children, shoe inserts and other hygiene articles to absorb bodily fluids. The composition of the present invention can also be used in other technical and industrial fields where liquids, in particular water or aqueous solutions, are absorbed. These fields are for example storage, packaging, transportation (as constituents of packaging material for water- or moisture-sensitive articles, for example for flower transportation, also as protection against mechanical impacts); animal hygiene (in cat litter); food packaging (transportation of fish, fresh meat; absorption of water, blood in fresh fish or meat packs); medicine (wound plasters, water-absorbing material for burn dressings or for other weeping wounds), cosmetics (carrier material for pharmachemicals and medicaments, rheumatic plasters, ultrasonic gel, cooling gel, cosmetic thickeners, sun protection); thickeners for oil-in-water and water-in-oil emulsions; textiles (moisture regulation in textiles, shoe inserts, for evaporative cooling, for example in protective clothing, gloves, headbands); chemical engineering applications (as a catalyst for organic reactions, to immobilize large functional molecules such as enzymes, as adhesion agent in relation to agglomerations, heat storage media, filter aids, hydrophilic component in polymeric laminates, dispersants, superplasticizers); as auxiliaries in powder injection moulding, in building construction and engineering (installation, in loam-based renders, as a vibration-inhibiting medium, auxiliaries in tunnel excavations in water-rich ground, cable sheathing); water treatment, waste treatment, water removal (deicing agents, reusable sandbags); cleaning; agritech (irrigation, retention of melt water and dew deposits, composting additive, protection of forests against fungal/insect infestation, delayed release of active components to plants); for firefighting or for fire protection; coextrusion agents in thermoplastic polymers (for example to hydrophilize multilayered films); production of films and thermoplastic mouldings able to absorb water (for example rain and dew water storage films for agriculture; superabsorbent-containing films for keeping fruit and vegetables fresh which are packed in moist films; superabsorbent-polystyrene coextrudates, for example for food packaging such as meat, fish, poultry, fruit and vegetables); or as carrier substance in formulations of active components (pharma, crop protection).

Superabsorbent Property Test Methods

Absorption Under Load 0.9 psi (AUL 0.9 psi)

The procedure for determining AUL 0.9 psi is disclosed in WO 00/62 825, pages 22-23 (referred to as "Absorbency Under Load" therein). A 317 gram weight is used to obtain the AUL 0.9 psi value.

Centrifuge Retention Capacity (CRC)

The method for determination of the Centrifuge Retention Capacity (CRC) is described in US patent application no. US 2002/0165288 A1, paragraphs [0105] and [0106].

Flow Rate

Flow Rate is determined using EDANA (European Disposbles and Nonwovens Association, Avenue Eugéne Plasky, 157, 1030 Brussels, Belgium, www.edana.org) Test Method 450.2-02 (available from EDANA).

Free Swell Gel Bed Permeability (Free Swell GBP)

The method for determination of the Free Swell Gel Bed Permeability (Free Swell GBP) is described in US patent application no. US 2005/0256757 A1, paragraphs [0061] through [0075].

Hausner Ratio

The Hausner Ratio is calculated from the Packed Bulk Density and the Apparent Bulk Density using the following equation:

$$\text{Hausner Ratio} = PBD/ABO$$

Apparent Bulk Density

The apparent bulk density ("ABD") of a superabsorbent material is determined by pouring a representative sample through a specified funnel into a density cup. The mass (g) of the sample in the cup is divided by the volume (mL) of the density cup to calculate the apparent bulk density of the polymer.

Equipment and Materials a. Funnel: with an orifice damper, according to German standard DIN 53492 b. Orifice internal diameter: 10.00 mm±0.01 mm c. Density cup, according to German standard DIN 53466
   Cylinder: 100.0 mL±0.5 ml capacity Cylinder internal diameter: 45.0 mm±0.1 mm
Cylinder internal height: 63.1 mm±0.1 mm
d. Spatula with a flat blade
e. Balance, accurate to ±0.01 g
f. Beaker, 250 mL capacity
g. Metal straight edge, flexible
h. Utility tray
i. Grounding wires with alligator clips General Keep samples in a closed containers and allow them to equilibrate to laboratory temperature before removing a sample for testing. Adjust laboratory conditions to 23±2° C. and 50±10% relative humidity. To obtain a representative sample, rotate the sample container end-over-end several times before taking a sample. The container should be no more than 80% full so as to ensure good mixing.

Procedure

Place the apparent gravity device into the utility tray which is placed on a stable, level surface. Center the funnel outlet 40 mm±1 mm above the density cup. Test each sample in duplicate on the same well-mixed laboratory sample. Ground the funnel and cup to avoid the build up of static electric charges. Weigh the empty density cup to the nearest 0.01 g and record the mass as W1. Weigh a 100.00 g±0.01 g sample of superabsorbent polymer into a 250 mL beaker. Pour the sample into the funnel with the orifice damper closed or use a metal straight edge to block the orifice. Open the orifice damper quickly or remove the metal straight edge quickly and allow the sample to completely fill and overflow the density cup. Use the spatula or straight edge to remove the excess superabsorbent by drawing it across the top of the density cup, being careful not to tap the density cup. Weigh the density cup containing the sample to the nearest 0.01 g and record the mass as W2. Do not use a brush on the funnel. Clean as needed with water and acetone. Dry after each use with a dry air jet.

Apparent Bulk Density Calculation

The apparent bulk density is calculated as follows:

$$ABD=(W2-W1)/V[g/mL]$$

where
W1=weight of empty density cup [g]
W2=weight of density cup with sample [g]
V=volume of the density cup (mL)

Calculate the arithmetic mean of the two individual test results. Report this mean result to the nearest 0.1 units accuracy, provided that the difference between the two individual results is not greater than 5% of the mean. If the difference is greater then 5%, repeat the tests in duplicate.

Packed Bulk Density

The packed bulk density ("PBD") of a superabsorbent material is determined by pouring a representative sample into a density cup. The cup is placed in a Powder Tester (Powder Characteristics Tester, Model PT-S, obtainable from Hosokawa Micron Powder Systems, Summit, N.J., U.S.A.), where it is tapped for a specified period of time. The mass of the sample in the cup is divided by the volume of the cup to calculate the packed bulk density of the polymer.

Equipment and Materials
a. Beaker, 250 ml
b. Balance, accurate to +0.01 g
c. Spatula with flat blade
d. Hosokawa Powder Tester, including 100 mL density cup and extension
e. Utility tray Hosokawa Powder Tester Setup Set the time to 180 sec on the 60 Hz scale, which equates to 1 tap per second. Set the "VIB/OFF/TAP" switch to "TAP". These settings should never be changed.

General

Keep samples in closed containers and allow them to equilibrate to laboratory temperature before removing a sample for testing. Adjust laboratory conditions to 23+/−2° C. and 50+/−10% relative humidity. To obtain a representative sample, rotate the sample container end over end several times before taking a sample. The container should be no more than 80% full so as to ensure good mixing.

Procedure

Test each sample in duplicate on the same well mixed laboratory sample. Weigh the empty density cup to the nearest 0.01 g and record the weight as W1. Weigh a 100 g+0.01 g sample into a 250 ml beaker. Place the Powder Tester's extension onto the density cup. Pour the sample into the density cup. Place the density cup onto the Powder Tester and press the "Start" button. When the tapping has stopped, remove the density cup and place it on the utility tray. Grasp the density cup firmly and remove the extension piece. Use a spatula to remove excess superabsorbent from the top of the density cup by scraping the top of the cup with the spatula. Weigh the density cup containing the sample to the nearest 0.01 g and record the weight as W2.

Packed Bulk Density Calculation

The packed bulk density (PBD) is calculated as follows:

$$PBD=(W2-W1)/V[g/mL]$$

Where:
W1=weight of empty density cup (g).
W2=weight of density cup with sample (g).
V=volume of density cup (mL)

Mass Flow

The mass flow test is designed to be indicative of the superabsorbent's conveying properties. A twin auger screw (pitch 48 mm, outer screw diameter 38.5 mm, inner screw diameter 15.5 mm, center-center screws distance 28.5 mm, screw-casing distance (clearing) 0.3 mm, length of screws 300 mm) equipped with an upstream hopper (40 liters volume, equipped with an agitator for avoiding product bridging) feeds into a receiving container placed on a scale. Superabsorbent is filled into the hopper and the twin screw operated at settings of 300 and 600 rpm. The amount of superabsorbent fed into the receiving container is continuously recorded.

EXAMPLES

Example 1

Polymer A 1040.00 g of glacial acrylic acid were added into a 4 liter glass reaction kettle equipped with a lid, thermocouple and nitrogen purge tube. Next, 3.12 g of pentaerythritol triallyl ether, 2430.17 g of de-ionised water, 3.83 g of Kymene® 736 (aqueous polyamidoamine epichlorohydrine adduct solution, obtained from Hercules Incorporated, Wilmington, Del. U.S.A.), and 500 g of ice made from deionized water were added. The monomer solution was then purged with nitrogen for 30 minutes. After 30 min, 11.44 g of 1 wt.-% aqueous hydrogen peroxide solution and 11.44 g of 1 wt.-% aqueous ascorbic acid solution were simultaneously added. After this initiation (the temperature rose rapidly and the monomer solution thickened), the purge tube was removed from the monomer solution and placed in the head space until the reaction temperature had peaked. The gel was kept overnight in an insulated container.

The gel was removed from the container and chopped once using a meat chopper (model 4812, manufactured by Hobart Corporation, Troy, Ohio, U.S.A.). 843.56 g of 50 wt.-% aqueous NaOH solution were added to the gel as evenly as possible. The gel was then kneaded thoroughly by hand and chopped twice using the Hobart meat chopper. Next, a solution of 10.40 g sodium metabisulfite in 200 g of deionized water was added to the gel as evenly as possible. The gel was again kneaded thoroughly by hand and chopped again twice using the Hobart meat chopper. The gel was then placed on a drum dryer (heated by steam, pressure >80 psi). The dried polymer flakes were collected and first crushed by hand, then milled using a pin mill (model ZM 200, manufactured by Retsch GmbH, Haan, Germany) at 14,000 rpm. The resulting powder was sifted to 850-160 micron using a sifter (model KS 1000, manufactured by Retsch GmbH, Haan, Germany) on setting 7 for ten minutes.

1 kg of the polymer powder was put into a mixer (laboratory ploughshare mixer model M 5, manufactured by Gebrüder Lödige Maschinenbau GmbH, Paderborn, Germany). A surface crosslinking solution was prepared by mixing 1.20 g of Denacol® EX 810 (ethylene glycol diglycidyl ether, obtained from Nagase ChemteX Corporation, Osaka, Japan), 20.00 g of propylene glycol, 20.00 g of deionized water, and 35.80 g of a 27 wt.-% aqueous aluminum sulfate solution into a beaker. At a mixer speed of 449 rpm, the surface crosslinker solution was added dropwise using a syringe to the polymer powder over a three minute time period. The mixer was than stopped, product sticking to the wall of the mixing vessel was scraped off (and re-united with the bulk), and mixing was continued for two more minutes at 449 rpm. The batch was then discharged into two stainless steel pans and placed in an oven at 120° C. for one hour. The pans the were removed from the oven and allowed to cool in a desiccator. The cooled product was then sifted, and the 850-150 micron cut designated Polymer A.

Example 2

Treatment of Polymer A with Cohesion Control Agent 1 kg of polymer A was placed in a stainless steel pan. Using a 3 ml syringe equipped with a needle, different amounts of polyethylene glycol 400 (polyethylene glycol of average molecular weight of 400 g/mol, "PEG-400") were added to the polymer, ensuring that the drops did not touch each other on the powder. The powder then was gently stirred with a spatula, carefully poured into a mixer (Lödige model M 5) and mixed for five minutes at 212 rpm.

PEG-400 amounts (wt.-ppm based on polymer A) and superabsorbent properties of the materials thus obtained are summarised in table 1.

TABLE 1

| PEG-400 [wt.-ppm] | CRC [g/g] | AUL 0.9 psi [g/g] | free swell GBP [Darcies] |
|---|---|---|---|
| 0 (polymer A) | 27.8 | 19.1 | 129 |
| 200 | 28.7 | 18.4 | 130 |
| 1000 | 28.5 | 18.3 | 117 |
| 2000 | 28.3 | 18.8 | 120 |
| 4000 | 28.5 | 18.0 | 134 |

Powder, flow and conveying properties are summarised in table 2.

TABLE 2

| PEG-400 [wt.-ppm] | PBD [g/ml] | ABD [g/ml] | Hausner Ratio | Flow Rate [g/s] | Mass flow at 300 rpm [kg/h] | Mass flow at 600 rpm [kg/h] |
|---|---|---|---|---|---|---|
| 0 (polymer A) | 0.843 | 0.737 | 1.14 | 11.7 | 709 | 1418 |
| 200 | 0.845 | 0.733 | 1.15 | 11.5 | 715 | 1423 |
| 1000 | 0.849 | 0.708 | 1.20 | 11.6 | 862 | 1715 |
| 2000 | 0.858 | 0.669 | 1.28 | 10.5 | 900 | 1782 |
| 4000 | 0.869 | 0.614 | 1.42 | no flow | 918 | 1818 |

Example 3

Polymer B

Polymer B was obtained following the procedure of Example 1, however, using the following amounts of chemicals:

1121.20 g of glacial acrylic acid
5.49 g of pentaerythritol triallyl ether,
2346.88 g of de-ionised water,
1.77 g of Kymene® 736
500 g of ice made from de-ionised water
12.33 g of 1 wt.-% aqueous hydrogen peroxide solution
12.33 g of 1 wt.-% aqueous ascorbic acid solution
909.42 g of 50 wt.-% aqueous NaOH solution
11.21 g sodium metabisulfite dissolved in 200 g of de-ionised water
0.60 g of Denacol® EX 810
20.00 g of propylene glycol
20.00 g of deionized water
35.80 g of 27 wt.-% aqueous aluminum sulfate solution Example 4

Treatment of Polymer B with Cohesion Control Agents

Following the procedure of example 2, samples of polymer B with various cohesion control agents and amounts thereof were obtained. Cohesion control agents used were PEG-400, 1,2-propylene glycol ("PG") and Silicone Oil (Type SF 96-100 obtained from GE Silicones, Wilton, Conn., U.S.A.). Amounts thereof (wt.-ppm based on polymer B), and superabsorbent properties of the materials thus obtained are summarised in table 3.

TABLE 3

| Cohesion Control Agent | Cohesion Control Agent amount [ppm] | CRC [g/g] | AUL 0.9 psi [g/g] | free swell GBP [Darcies] |
|---|---|---|---|---|
| 0 (polymer B) | 0 | 30.2 | 19.2 | 72 |
| PEG-400 | 500 | 30.3 | 18.9 | 75 |
| PEG-400 | 1000 | 30.5 | 19.2 | 73 |
| PEG-400 | 1500 | 30.3 | 19.1 | 68 |
| PEG-400 | 2000 | 30.2 | 20.0 | 69 |
| PEG-400 | 3000 | 30.3 | 18.3 | 65 |
| PG | 1000 | 30.5 | 19.2 | 70 |
| PG | 1500 | 30.3 | 19.1 | 71 |
| PG | 2000 | 30.3 | 18.9 | 69 |
| PG | 3000 | 30.2 | 18.3 | 70 |

TABLE 3-continued

| Cohesion Control Agent | Cohesion Control Agent amount [ppm] | CRC [g/g] | AUL 0.9 psi [g/g] | free swell GBP [Darcies] |
|---|---|---|---|---|
| Silicon oil | 1000 | 30.4 | 18.6 | 74 |
| Silicon oil | 2500 | 30.3 | 18.4 | 76 |

Powder, flow and conveying properties are summarised in table 4.

TABLE 4

| Cohesion Control Agent | Cohesion Control Agent amount [ppm] | PBD [g/ml] | ABD [g/ml] | Hausner Ratio | Flow Rate [g/s] | Mass flow at 300 rpm [kg/h] | Mass flow at 600 rpm [kg/h] |
|---|---|---|---|---|---|---|---|
| 0 (polymer B) | 0 | 0.859 | 0.753 | 1.14 | 12.0 | 692 | 1363 |
| PEG-400 | 500 | 0.870 | 0.717 | 1.21 | 11.7 | 882 | 1746 |
| PEG-400 | 1000 | 0.877 | 0.682 | 1.29 | 11.2 | 925 | 1832 |
| PEG-400 | 1500 | 0.879 | 0.662 | 1.33 | 10.4 | 940 | 1871 |
| PEG-400 | 2000 | 0.881 | 0.645 | 1.36 | no flow | 945 | 1871 |
| PEG-400 | 3000 | 0.880 | 0.622 | 1.41 | no flow | 947 | 1873 |
| PG | 1000 | 0.866 | 0.697 | 1.24 | 11.0 | 901 | 1784 |
| PG | 1500 | 0.866 | 0.676 | 1.28 | 10.7 | 923 | 1832 |
| PG | 2000 | 0.862 | 0.659 | 1.31 | 10.3 | 936 | 1862 |
| PG | 3000 | 0.865 | 0.632 | 1.37 | no flow | 950 | 1881 |
| Silicon oil | 1000 | 0.892 | 0.726 | 1.23 | 12.6 | 905 | 1801 |
| Silicon oil | 2500 | 0.888 | 0.695 | 1.28 | 11.3 | 928 | 1846 |

Example 5

Polymer C

A kneader with two sigma shafts (Model LUK 8.0 K2 manufactured by Coperion Werner & Pfleiderer GmbH & Co. KG, Stuttgart, Germany) was purged with nitrogen and filled with a nitrogen flushed mixture of 5166 g of a 37.7 wt.-% aqueous solution of sodium acrylate, 574 g of acrylic acid and 720 g of deionized water. Subsequently, 10.7 g of ETMPTA (ethoxylated trimethylolpropane triacrylate, on average 15 mol of ethylene oxide per mol of trimethylolpropane), 10 g of a 0.75 wt.-% aqueous ascorbic acid solution, 16.6 g of a 15 wt.-% aqueous sodium persulfate solution and 3.75 g of a 3 wt.-% aqueous hydrogen peroxide solution were added. The kneader was operated at maximum speed of 98 rpm of one shaft and 49 rpm of the other. Directly after the addition of hydrogen peroxide the solution was heated by starting to circulate hot oil (80° C.) through the heating jacket. After the peak temperature was reached the heating was stopped and the polymer gel was allowed to react for another 14 minutes. Subsequently the gel was cooled down to approximately 65° C. and placed on a tray. The gel was dried in an oven at 170° C. for 75 min (approx. 1000 g of gel per tray). Finally the dried gel was milled three times by means of a roller mill (model LRC 125/70 manufactured by Bauermeister Zerkleinerungstechnik GmbH, Norderstedt, Germany), using gap sizes of 1000 μm, 600 μm and 400 μm. The product was then sifted, and the 850-150 micron cut selected.

1 kg of this polymer powder was treated using a Lödige M5 mixer with 1.72% of a surface crosslinker solution consisting of 0.12 wt.-% ethylene diglycidyl ether, 1.0 wt.-% water and 0.6 wt.-% of 1,2-propandiol via atomizer nozzle. Subsequently 3.1 wt.-% of a 17 wt.-% aqueous aluminium sulphate solution were added the same way. The mixture was heated for one hour at 180° C. and then cooled to room temperature. The cooled product was then sifted, and the 850-150 micron cut designated Polymer C.

Example 6

Treatment of Polymer C with Cohesion Control Agent 1 kg of polymer C was filled in a Lödige M5 mixer and rotated at 200 rpm. An atomizer nozzle was used to spray a mixture of 4 parts of de-ionised water and 1 part of PEG-400 at ambient temperature onto the polymer. Afterwards the polymer was mixed for additional 5 min at 69 rpm, and finally sifted. The 850-105 micron cut was selected.

PEG-400 amounts (wt.-ppm based on polymer C) and superabsorbent properties of the materials thus obtained are summarised in table 5.

TABLE 5

| PEG-400 [ppm] | CRC [g/g] | AUL 0.9 psi [g/g] | Free swell GBP [Darcies] |
|---|---|---|---|
| 0 (polymer C) | 26.6 | 20.5 | 68 |
| 500 | 27.2 | 21.1 | 68 |
| 700 | 27.0 | 20.8 | 67 |
| 1000 | 26.8 | 20.6 | 69 |

Powder, flow and conveying properties are summarised in table 6.

TABLE 6

| PEG-400 [ppm] | PBD [g/ml] | ABD [g/ml] | Hausner Ratio | Flow Rate [g/s] | Mass flow at 300 rpm [kg/h] | Mass flow at 600 rpm [kg/h] |
|---|---|---|---|---|---|---|
| 0 (polymer C) | 0.835 | 0.739 | 1.13 | 11.2 | 680 | 1321 |
| 500 | 0.837 | 0.688 | 1.22 | 11.0 | 811 | 1630 |
| 700 | 0.841 | 0.673 | 1.25 | 10.8 | 857 | 1697 |
| 1000 | 0.846 | 0.651 | 1.30 | 10.5 | 883 | 1757 |

Example 7

Polymer D 92.4 g of acrylic acid, 0.022 g of pentaerythritol triallyl ether and 87.2 g of de-ionised water were mixed. 40.4 g of sodium carbonate were added, the temperature of the monomer solution was maintained below 30° C. during this neutralization reaction. Then, 0.081 g of 2,2'-azobisamidinopropane dihydrochloride and 0.054 g of hydrogen peroxide were mixed into the monomer mixture. The mixture was then heated to 62° C. and poured into a pan. 0.027 g of Brüggolit® FF6 (a sodium salt of a sulfinic acid derivative, obtained from L. Brüggemann KG, Heilbronn, Germany), dissolved in 5 g of de-ionised water, were added to initiate the polymerization. Due to the heat of polymerization the major part of the water evaporated during the reaction, and at the end a polymer mass with a residual moisture content of about 15 wt.-% was obtained. The polymer mass was dried in a drying oven at 120° C., milled and classified to a particle size distribution of 106-850 μm. The dry powder was blended with 0.25 wt.-% of hydrophobic silica (Sipernat® D-17 obtained from Degussa AG, Frankfurt, Germany) and then surface crosslinked by spraying a solution consisting of (wt.-% based on polymer powder) 0.46 wt.-% of Denacol® EX 810, 7.26 wt.-% of water and 2.29 wt.-% of 1,3-propandiol onto the particles and subsequent curing at 120° C. for one hour. The powder obtained was designated polymer D.

Example 8

Treatment of Polymer D with Cohesion Control Agents

Following the procedure of example 2, samples of polymer D treated with PEG-400 were obtained. PEG-400 amounts (wt.-ppm based on polymer D) and superabsorbent properties of the materials thus obtained are summarised in table 7.

TABLE 7

| PEG-400 [ppm] | CRC [g/g] | AUL 0.9 psi [g/g] | Free swell GBP [Darcies] |
|---|---|---|---|
| 0 (polymer D) | 28.9 | 17.6 | 30 |
| 500 | 28.8 | 17.0 | 31 |
| 1000 | 28.4 | 17.3 | 29 |
| 1500 | 29.2 | 17.4 | 29 |
| 3000 | 28.9 | 17.0 | 27 |

Powder, flow and conveying properties are summarised in table 8.

TABLE 8

| PEG-400 [ppm] | PBD [g/ml] | ABD [g/ml] | Hausner Ratio | Flow Rate [g/s] | Mass flow at 300 rpm [kg/h] | Mass flow at 600 rpm [kg/h] |
|---|---|---|---|---|---|---|
| 0 (polymer D) | 0.833 | 0.724 | 1.15 | 10.9 | 702 | 1399 |
| 500 | 0.834 | 0.659 | 1.27 | 10.3 | 873 | 1709 |
| 1000 | 0.842 | 0.621 | 1.36 | no flow | 891 | 1727 |
| 1500 | 0.850 | 0.602 | 1.41 | no flow | 909 | 1745 |
| 3000 | 0.854 | 0.587 | 1.46 | no flow | 927 | 1782 |

The examples clearly demonstrate that a superabsorbent according to this invention exhibits superior GBP and flow characteristics.

We claim:

1. A superabsorbent comprising a permeability enhancing agent and a cohesion control agent and having a free swell gel bed permeability of at least 15 Darcies and a Hausner ratio in the range of 1.18 to 1.34.

2. The superabsorbent of claim 1, in which the permeability enhancing agent is at least one agent selected from the group consisting of particulate inorganic or organic solids, cationic polymers, and water-soluble polyvalent metal salts.

3. The superabsorbent of claim 2, in which the permeability enhancing agent comprises silica and/or aluminium sulphate.

4. The superabsorbent of claim 1, which comprises a permeability enhancing agent in an, amount in the range of 0.05 wt.-% to 5 wt.-%, based on the total weight of the superabsorbent.

5. The superabsorbent of claim 1, in which the cohesion control agent is at least one non-aqueous liquid having a viscosity of at least 20 mPas which is selected from the group consisting of alcohols, polyglycols, silicon oils, hydrophilic modified silicon oils, and paraffin oils.

6. The superabsorbent of claim 5, in which the cohesion control agent is polyethylene glycol of an average molecular weight of less than 1,500 g/mol.

7. The superabsorbent of claim 6, which comprises a cohesion control agent in an amount in the range of 100 wt.-ppm to 5,000 wt.-ppm, based on the total weight of superabsorbent.

8. A process for producing the superabsorbent defined in claim 1, in which 0.05 wt.-% to 5 wt.-% permeability enhancing agent, based on the total weight of the superabsorbent, and 100 wt.-ppm to 5,000 wt.-ppm cohesion control agent, based on the total weight of superabsorbent, are added during the production process.

9. A hygiene article comprising the superabsorbent of claim 1.

* * * * *